US00PP37580P2

(12) United States Plant Patent
Barr

(10) Patent No.: US PP37,580 P2
(45) Date of Patent: Aug. 11, 2026

(54) ***ACER* PLANT NAMED 'EVERBRAZOS'**

(50) Latin Name: *Acer rubrum*
Varietal Denomination: EVERBRAZOS

(71) Applicant: TYFCO LLC, Houston, TX (US)

(72) Inventor: William C Barr, Rosenberg, TX (US)

(73) Assignee: TYFCO LLC, Houston, TX (US)

( * ) Notice: Subject to any disclaimer, the term of this patent is extended or adjusted under 35 U.S.C. 154(b) by 0 days.

(21) Appl. No.: 19/352,761

(22) Filed: Oct. 8, 2025

(51) Int. Cl.
*A01H 6/00* (2018.01)
*A01H 5/12* (2018.01)

(52) U.S. Cl.
USPC ..... Plt./224

(58) Field of Classification Search
USPC ..... Plt./224
CPC ..... A01H 6/00; A01H 5/12
See application file for complete search history.

*Primary Examiner* — Keith O. Robinson
(74) *Attorney, Agent, or Firm* — Penny J. Aguirre

(57) ABSTRACT

A new cultivar of *Acer rubrum* tree named 'EVERBRAZOS' that is characterized by its foliage with new growth that is red color that continues from spring through fall, its foliage colors ranging from red appearing on about 60 cm on the end of the branch, with mid-section of branch yellow-green, and lower section of branch (mature) green in color, its tolerance to the low number of chilling hours observed in Glen Flora, Texas with strong branches and a lack of branch die back, its tolerance to the low number of chilling hours observed in Glen Flora, Texas with strong branches and a lack of branch die back, average height of 7 m and average width of 4 m as a 5-year-old plant, its success rate of rooting unrooted cuttings of approximately 95%.

3 Drawing Sheets

Botanical classification: *Acer rubrum.*
Variety denomination: 'EVERBRAZOS'.

BACKGROUND OF THE INVENTION

The present invention relates to a new and distinct cultivar of *Acer rubrum* and will be referred to hereafter by its cultivar name, 'EVERBRAZOS'. 'EVERBRAZOS' is a deciduous tree grown for use as a landscape plant.

The new cultivar was discovered in spring of 2016 as a whole plant mutation that arose in a production field planted with unnamed and unpatented plants of *Acer rubrum* in Rosenberg, Texas. The parent plants are therefore unknown.

Asexual propagation of the new cultivar was first accomplished by cuttings under the direction of the Inventor in Glen Flora, Texas in 2016. Asexual propagation by cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'EVERBRAZOS' as a new and unique cultivar of *Acer.*

1. 'EVERBRAZOS' exhibits foliage with new growth that is red color that continues from spring through fall.
2. 'EVERBRAZOS' exhibits foliage colors ranging from red appearing on about 60 cm on the end of the branch, with mid-section of branch yellow-green, and lower section of branch (mature) green in color.
3. 'EVERBRAZOS' exhibits a tolerance to the low number of chilling hours observed in Glen Flora, Texas with strong branches and a lack of branch die back.

4. 'EVERBRAZOS' exhibits an average height of 7 m and average width of 4 m as a 5-year-old plant.
5. 'EVERBRAZOS' exhibits a success rate of rooting unrooted cuttings of approximately 95%.

The plants of *Acer rubrum* grown in the field of discovery are similar to 'EVERBRAZOS' in mature leaf coloration and plant size. The plants of *Acer rubrum* grown in the field of discovery differs from 'EVERBRAZOS' in having just a red flush on new growth with young foliage quickly turning green in color and in typically exhibiting branch die back and a short lifespan due to the lack of chilling hours in Glen Flora, Texas. 'EVERBRAZOS' can be compared to the *Acer rubrum* cultivar 'Florida Flame' (not patented). 'Florida Flame' is similar to 'EVERBRAZOS' in leaf morphology and growth habit. 'Florida Flame' differs from 'EVERBRAZOS' in having foliage with red new growth observed only in the first spring flush with subsequent new growth throughout the summer and fall green in color.

BRIEF DESCRIPTION OF THE DRAWINGS

The accompanying color photographs illustrates the overall appearance and distinct characteristics of 5-year-old trees of the new cultivar as grown outdoors in 3-gallon containers in Glen Flora, Texas.

The photograph in FIG. 1 provides a view of a group of plants of 'EVERBRAZOS' and provides a view of the changing foliage colors.

Figure 1:
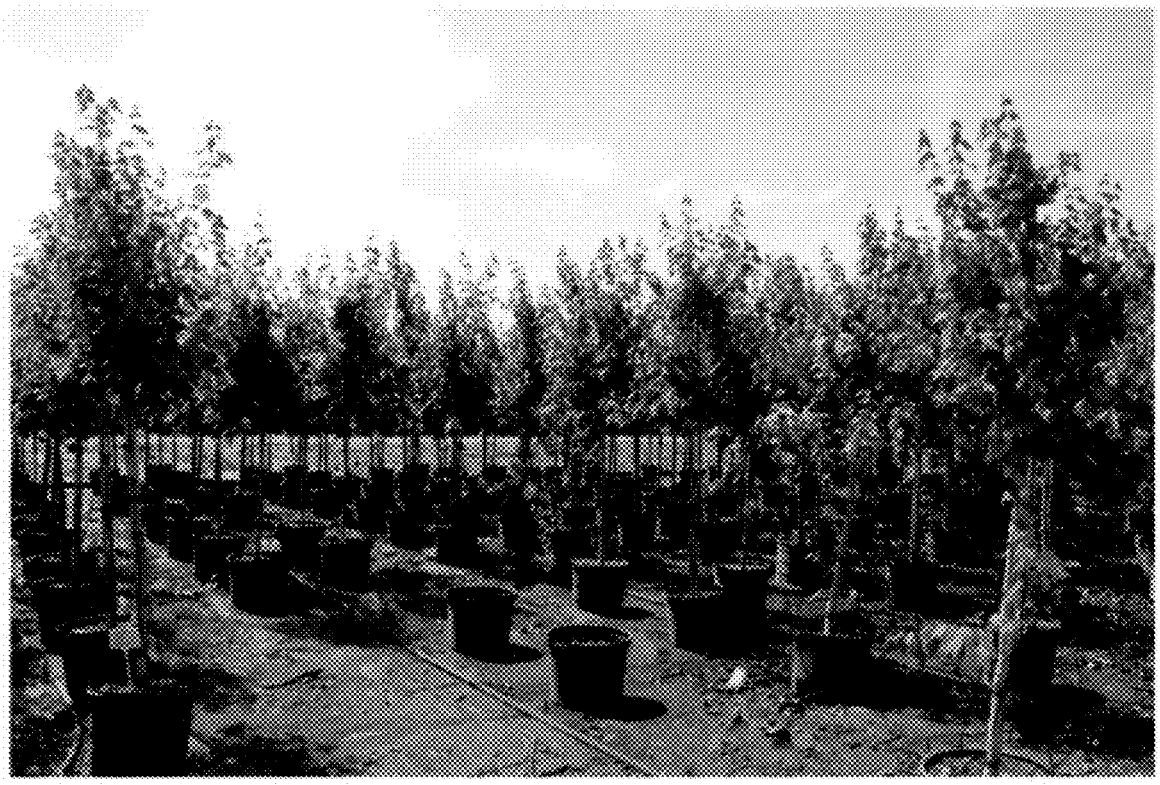
Figure 2:
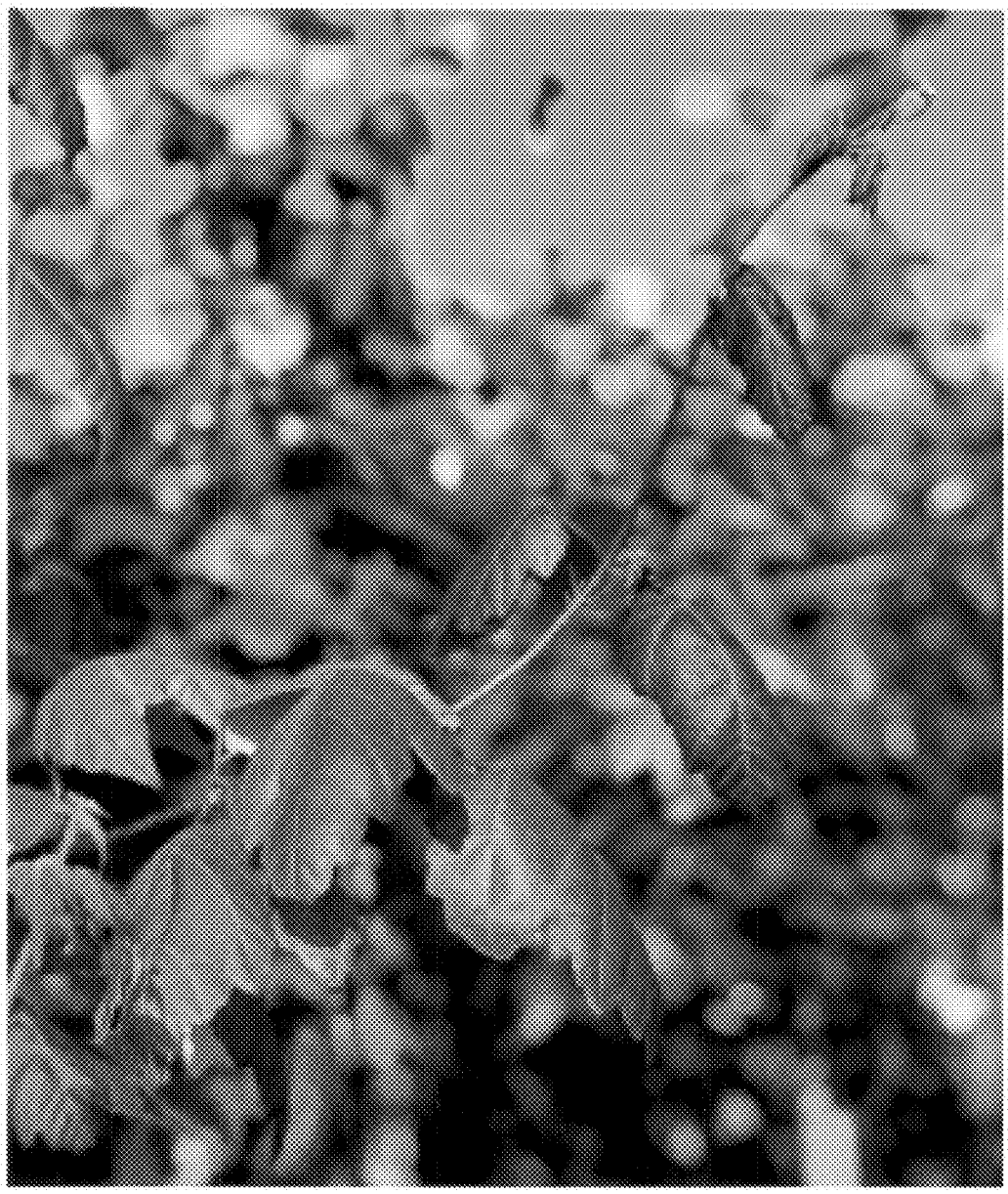

The photograph in FIG. 2 provides a close-up view of a branch of 'EVERBRAZOS'.

Figure 3:
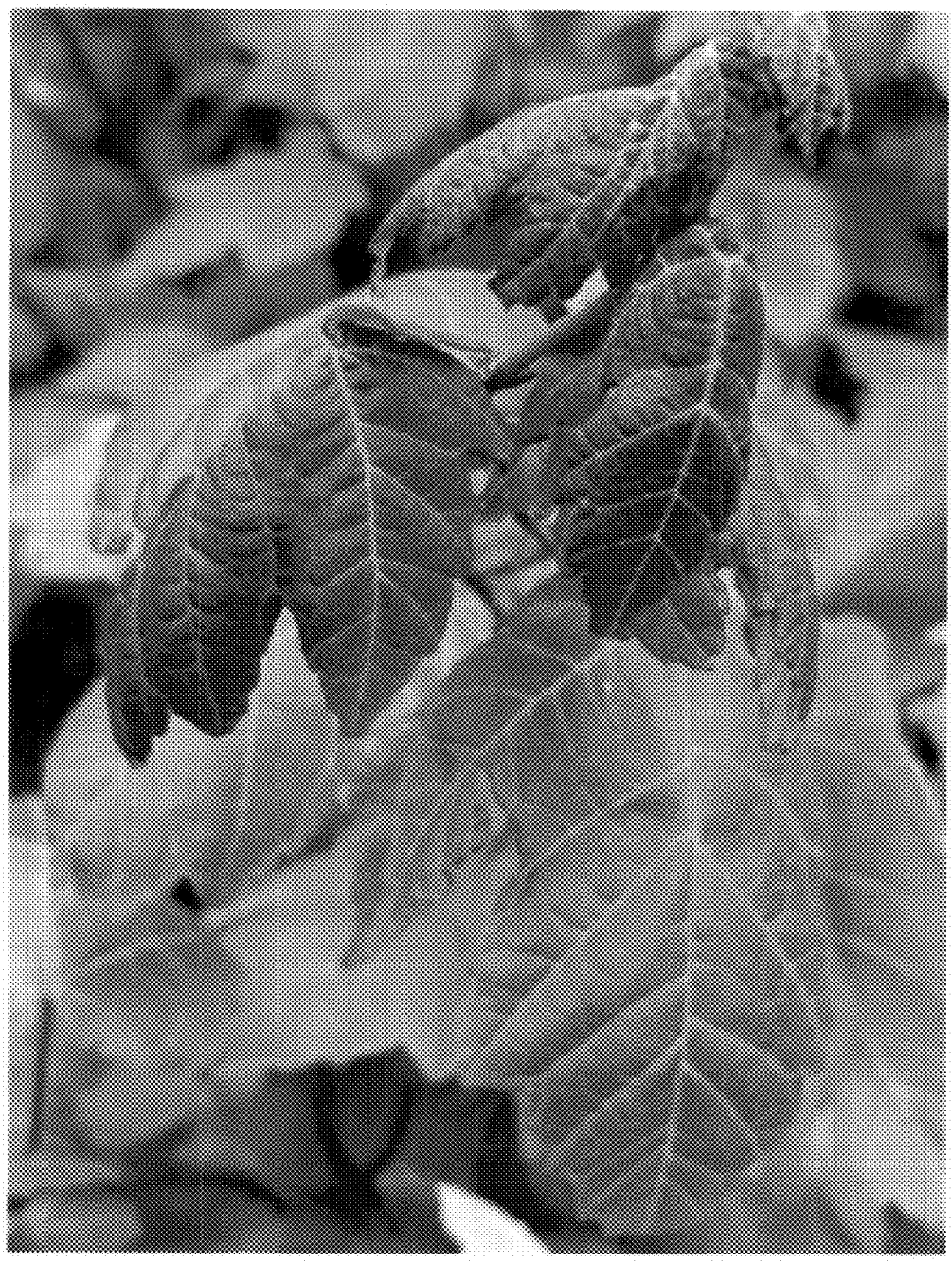

The photograph in FIG. 3 provides a close-up view of the new leaves of 'EVERBRAZOS'.

The colors in the photographs may differ slightly from the color values cited in the detailed botanical description, which accurately describe the colors of the new *Acer.*

DETAILED BOTANICAL DESCRIPTION

The following is a detailed description of 3-year-old trees of the new cultivar as grown in outdoors in 3-gallon containers in Glen Flora, Texas. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Deciduous tree.

*Plant habit*.—Upright.

*Height and spread*.—An average of 7 m in height and 4 m in spread as a 5-year-old plant as grown in a container.

*Hardiness*.—At least in U.S.D.A. Zones 3 to 9, the new cultivar thrives in U.S.D.A. Zone 9, which is not typical for plants of *Acer rubrum*.

*Diseases and pests*.—No susceptibility or resistance to diseases or pest has been observed.

*Root description*.—Fibrous, freely branched, 199A and 200A in color.

*Propagation*.—Cuttings.

*Root development*.—Time required for root initiation is 6 to 12 weeks, time required to produce a young plant cutting is 6 to 9 months from a rooted liner to a 1-gallon-trade container.

*Growth rate*.—Vigorous with fast growth in spring into the summer.

Branch description:

*Branch shape*.—Round.

*Branch size*.—Main; 1.5 m in length, an average of 1 cm in diameter, lateral; an average of 26 cm in length and 4 mm in diameter.

*Branch surface*.—Slightly glossy, moderately covered with lenticels.

*Branch color*.—Young; 144A, flushed with 182A, mature; 148A, older; 198A.

*Branch strength*.—Strong.

*Branch aspect*.—Main; vertical, lateral; held in multiple angles.

*Internode length*.—An average of 13 cm.

*Branching*.—Main; 1, lateral; 30 per main.

Foliage description:

*Leaf shape*.—Palmately lobed, reniform to orbicular in outline.

*Leaf division*.—Simple.

*Leaf base*.—Truncate.

*Leaf apex*.—Acute, outer tip mucronate.

*Leaf fragrance*.—None.

*Leaf venation*.—Palmate, young leaves upper and lower surface color; 149A, mature upper and lower surface color; 150C, slightly flushed with 184A.

*Leaf quantity*.—An average of 16 per lateral branch.

*Leaf margins*.—Palmately 5-lobed, lobe margins serrate with 2 to 4 teeth per lobe, sinus depth moderately deep, sinus orientation is convergent.

*Leaf arrangement*.—Opposite.

*Leaf aspect*.—Slightly downward and cupped.

*Leaf attachment*.—Petiolate.

*Leaf surface*.—Both surfaces matte, glabrous.

*Leaf size*.—Average of 14 cm in length and 13 cm in width.

*Leaf color*.—Young upper and lower surface spring through fall; N45B to N45D, maturing upper and lower surface; 145A to 145C, mature upper and lower surface N138A to N138C, fall color, both surfaces 182A and 185A.

*Petioles*.—Average of 6 cm in length and 2 mm in diameter, surface glabrous, smooth and slightly glossy, strong, color, 144A, flushed with 182A.

*Stipules*.—None.

Inflorescence description: None observed to date.

Fruit and seed: None observed to date.

It is claimed:

1. A new and distinct cultivar of *Acer rubrum* tree named 'EVERBRAZOS' as herein illustrated and described.

* * * * *